Figure 1:
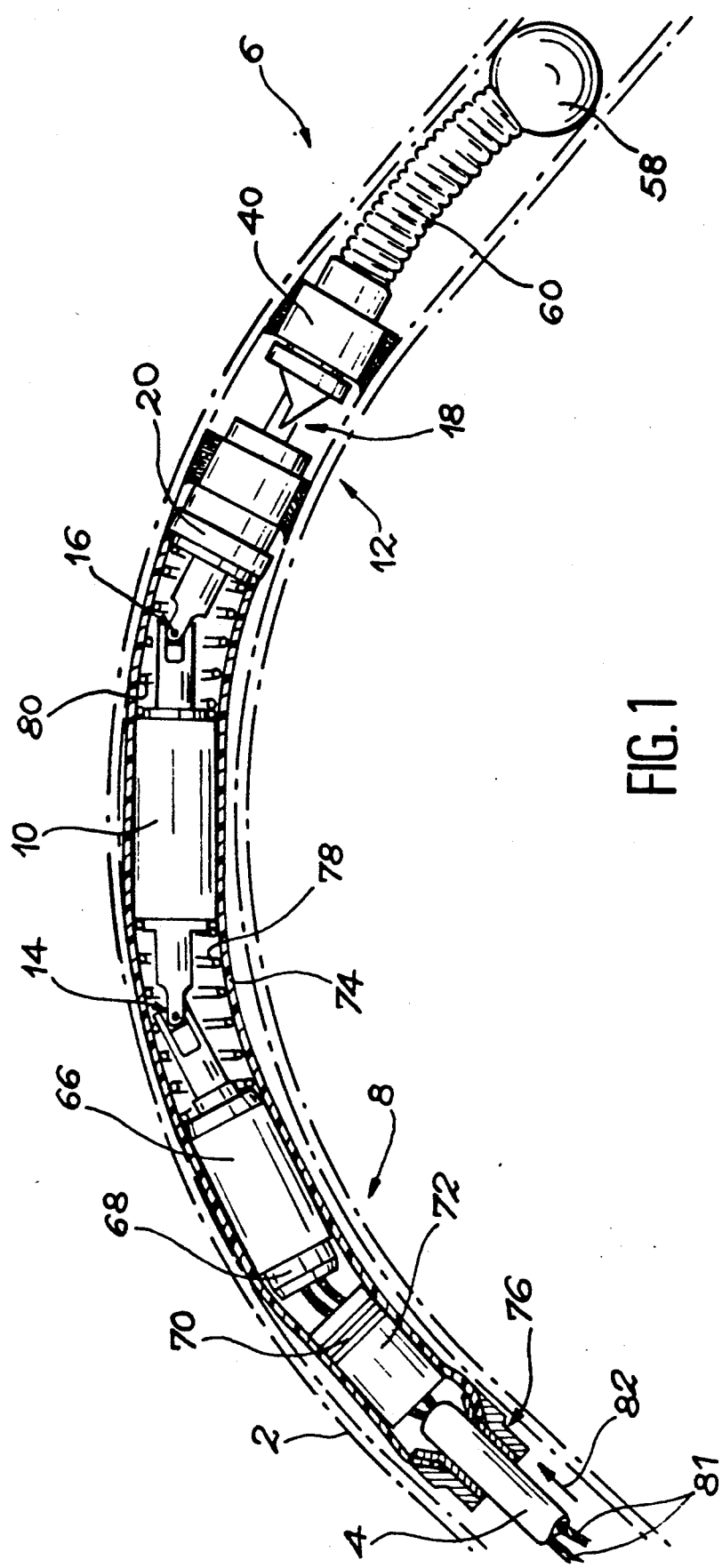

United States Patent [19]

Gondard et al.

[11] Patent Number: 5,313,838

[45] Date of Patent: May 24, 1994

[54] BENT TUBE INSPECTION PROBE WITH A ROTARY INSPECTION HEAD

[75] Inventors: Christian Gondard, Epinay sur Orge; Bernard Stockmann, Genevieve des Bois; Jacky Viard, Orsay, all of France

[73] Assignee: Commissariat A L'Energie Atomique, Paris, France

[21] Appl. No.: 784,375

[22] Filed: Oct. 29, 1991

[30] Foreign Application Priority Data

Oct. 31, 1990 [FR] France ................. 90 13530

[51] Int. Cl.⁵ .................................. G01N 29/24
[52] U.S. Cl. ........................... 73/623; 324/220; 324/226; 376/249; 376/252
[58] Field of Search ............. 73/620, 623, 629, 644; 324/220, 219, 221, 226; 376/249, 252

[56] References Cited

U.S. PATENT DOCUMENTS

| | | | |
|---|---|---|---|
| 3,483,466 | 12/1969 | Crouch et al. | 324/220 |
| 4,153,875 | 5/1979 | Pigeon et al. | 324/220 |
| 4,412,315 | 10/1983 | Flournoy | 73/623 |
| 4,460,920 | 7/1984 | Weber et al. | 73/623 |
| 4,807,484 | 2/1989 | Goedecke | 73/866.5 |

FOREIGN PATENT DOCUMENTS

| | | |
|---|---|---|
| 0105418 | 4/1984 | European Pat. Off. |
| 0147648 | 7/1985 | European Pat. Off. |
| 0255619 | 8/1986 | European Pat. Off. |
| 0259669 | 3/1988 | European Pat. Off. |
| 0301906 | 2/1989 | European Pat. Off. |
| 0318387 | 5/1989 | European Pat. Off. |
| 2136259 | 1/1972 | Fed. Rep. of Germany |
| 2640055 | 3/1978 | Fed. Rep. of Germany |
| 0109490 | 8/1979 | Japan .................... 73/623 |

OTHER PUBLICATIONS

"IRIS—Internal Rotary Inspection System" by M. E. Rentler, Materials Evaluation (Jul. 1983) pp. 884-886.

Primary Examiner—Hezron E. Williams
Assistant Examiner—Rose M. Finley
Attorney, Agent, or Firm—Michael N. Meller

[57] ABSTRACT

This probe comprises a cable (4) and a probe head (6) fixed to one end of the cable and having an inspection head (18) provided with transmission-reception means (22, 24) for inspection signals from a tube (2), a support (20) on which the inspection head is mounted in rotary manner, a motor (66) for rotating the inspection head, an encoder associated with the motor for determining the circumferential extent of faults which the tube may have, and a rotary collector (10) between the motor and the support in order to ensure a mechanical connection between the motor and the inspection head and the transmission of control signals for the said means (22, 24) and signals supplied by the latter. Articulated mechanical connections (14, 16) are provided between the motor and the collector and between the collector and the inspection head. A sheath which is flexible in flexion and rigid in torsion join together the support, the stator of the motor and the stator of the collector and prevents circumferential displacements thereof. Application to the inspection of heat exchanger tubes.

10 Claims, 2 Drawing Sheets

BENT TUBE INSPECTION PROBE WITH A ROTARY INSPECTION HEAD

DESCRIPTION

The present invention relates to a bent tube inspection probe. It more particularly applies to the inspection of heat exchanger tubes and in particular the inspection of tubes of steam generators equipping nuclear reactors.

The following documents disclose bent tube inspection probes:
(1) French patent application 75 24 698 of 7.8.1975 (cf. also U.S. Pat. No. 4,153,875)
(2) French patent application 83 00692 of 18.1.1983 (cf. also U.S. Pat. No. 4,633,177)
(3) GB-A-1 453 189
(4) Inspection of steam generator tubes with ultrasonic techniques, the NUCON NERASON SYSTEM Document No. 19530-00-003, Issue No. 4, August 1987, Nucon Company, Netherlands.

In particular, document (4) describes a bent tube inspection probe having an inspection head incorporating a transmitting-receiving ultrasonic transducer mounted in fixed manner on a first support member, a rotary mirror mounted on a second support member facing the first support member and connected thereto by an intermediate part, the mirror permitting the reflection of the ultrasonics emitted by the latter towards a tube to be inspected and into which is introduced the probe and a motor placed in the second support member and rotating the mirror.

This known probe has two disadvantages:

a) The rotary ultrasonic beam from the mirror is periodically obscured by the part interconnecting the two support members, which creates dead zones on the inner surface of the tube to be inspected. In order to get round this problem, the probe has a supplementary head having the same structure as the preceding probe head, but an orientation opposed thereto, so that the dead zones which it creates are at 180° from those created by the preceding probe head, which leads to a complicated overall probe.

b) The inhomogeneities of the transducer lead in the known probe head structure to distortions on the inspection signals supplied by the probe.

The present invention aims at obviating the first of these disadvantages and in a special embodiment the second disadvantage. Moreover, the present invention solves the problem of the precise pinpointing of faults in tubes in the circumferential direction.

The present invention specifically relates to a bent tube inspection probe, which is introduced into a tube to be inspected and has a cable provided with electrical conductors and a probe head fixed to one end of the cable and which has an inspection head with transmission-reception means for tube inspection signals, said probe being characterized in that the probe head also comprises a support on which the inspection head is mounted in rotary manner, a motor for rotating the inspection head, an encoder associated with the motor and serving to determine the circumferential extension of faults which the tube may have and a rotary collector positioned between the motor and the support and which ensures a mechanical connection between the motor and the inspection head, as well as the transmission of electrical control signals for the transmission-reception means and electrical signals supplied by the latter and in that articulated mechanical connections are provided respectively between the motor and the rotary collector and between the rotary collector and the inspection head and in that the probe also comprises a sheath which is flexible in flexion and rigid in torsion and which joins together the said support, the stator of the motor and the stator of the rotary collector and prevents relative circumferential displacements thereof.

It is thus possible to accurately pinpoint the faults of tubes in the circumferential direction, because the sheath renders integral the support, the motor stator and the collector stator. Without the sheath, these parts would be mechanically disengaged from one another and would be subject to relative circumferential displacements leading to imprecision with respect to the pinpointing of faults, so that signal processing software would become unusable.

In addition, these relative displacements would be liable to damage and even fracture the electrical wires joining the cable to the rotary collector stator and carrying the measurement signals.

It should be noted that the sheath used in the present invention is very different from a bellows, which is also flexible in flexion and rigid in torsion, but which has large overall dimensions. It is also very difficult to tightly join a bellows to the stators of the motor and the collector. Finally, it prevents the indispensable access to the members located inside the same (electrical wires, cardan joints, etc.).

Admittedly, EP-A-0 301 906 (Westinghouse Electric Corporation) discloses a tube inspection probe having three elements, namely a motor, a rotary collector and an ultrasonic transducer support, whose respective stators are rendered integral with one another with the aid of a rigid casing. However, this rigidity of the casing prevents the passage of bent tubes.

According to the present invention, it is possible to introduce tubes, whose radius of curvature is roughly five times the mean diameter of the tubes.

In the probe according to the invention, the inspection head assembly is rotary. No support obscures the signals from the transmission-reception means and there is no dead zone.

According to an embodiment of the probe according to the invention, the transmission-reception means incorporate an ultrasonic transmitting-receiving transducer and ultrasonic reflection means positioned facing the transducer and rendered integral therewith and which serve to reflect the ultrasonics emitted by the transducer towards the tube and for reflecting towards said transducer the ultrasonics from the tube.

In this special embodiment, the transducer and the ultrasonic reflection means form a rigid assembly, which eliminates the inhomogeneity effects of the ultrasonic beam emitted by the transducer and which occur in the probe of document (4) due to inhomogeneities of its ultrasonic transducers.

The rotary movement of the motor is transmitted to said rigid assembly via the rotary collector.

It can be seen that no equipment support obscures the ultrasonic beam from the ultrasonic reflection means and consequently dead zones are eliminated.

Moreover, the use of ultrasonic reflection means in the present invention makes it possible to use a larger ultrasonic transmitting-receiving transducer and to move it away from the inner wall of a tube to be inspected. Thus, an inspection is carried out, whose quality is better than that of inspections carried out with probes not having such ultrasonic reflection means. In these probes, the transducer is positioned too close to the inner wall of the tube and its dimensions are very small, which is prejudicial to the quality of the inspection.

An advantage of the present invention is the possibility of replacing the ultrasonic inspection head incorporating the transducer and the ultrasonic reflection means by an eddy current inspection head. In this case, the transmission-reception means comprise a transmitting-receiving coil for the inspection of the tube by eddy currents. The probe head can also have an auxiliary coil for revealing by means of eddy currents breaks in the tube or its environment, so that it is possible to identify the position of the inspection head in the tube. This makes it possible to draw up a fault "map". The probe can be moved within the tube by means of a flow of water.

In the case of an ultrasonic inspection, this water can also constitute the coupling medium between the ultrasonic transducer, the ultrasonic reflection means associated with said transducer and the inner wall of the tube. This gives an ultrasonic inspection probe simpler than the probe marketed by NUCON (cf. document (4)).

Thus, for the latter probe, the propulsion is pneumatic and the coupling liquid between each ultrasonic transducer, the ultrasonic reflection means corresponding thereto and the inner wall of a tube to be inspected is transported from the exterior of the tube to be inspected to the transducer by a duct located within the cable and which links the two probe heads to control means positioned externally of the tube to be inspected.

The sheath used in the invention can also be electrically insulating and tight and can trap at least that part of the probe head passing from the motor to the support on which the inspection head is mounted in rotary manner.

Such a sheath is of particular interest when the probe according to the invention is displaced in the tube by means of a stream of water, because it then ensures the electrical insulation of the members permitting the rotation of the inspection head with respect to their environment.

The sheath can be made from an elastomer material and can be formed on a braided support. This elastomer material can be silicone.

Finally, each of the mechanical connections or links between the motor and the rotary collector and between the latter and the inspection head can comprise a homokinetic joint, e.g. a cardan joint.

The invention is described in greater detail hereinafter relative to non-limitative embodiments and the attached drawings, wherein show:

FIG. 1 A diagrammatic view of a special embodiment of the probe according to the invention permitting an inspection of bent tubes by ultrasonics.

Figure 2:
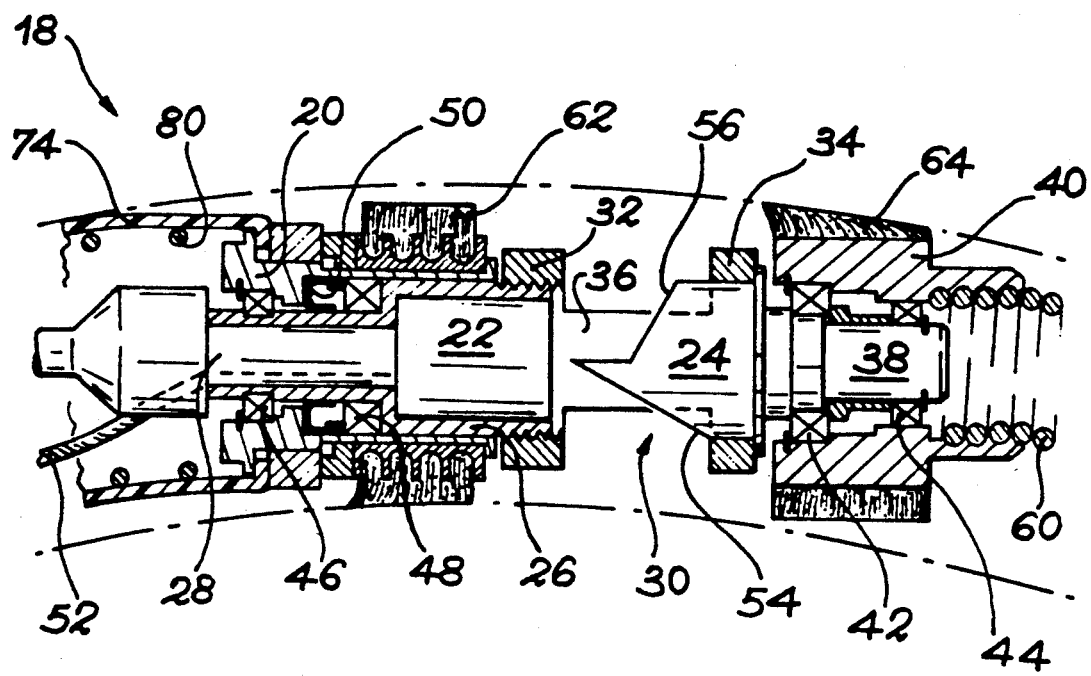

FIG. 2 A sectional view diagrammatically illustrating the inspection head incorporating the probe shown in FIG. 1.

Figure 3:
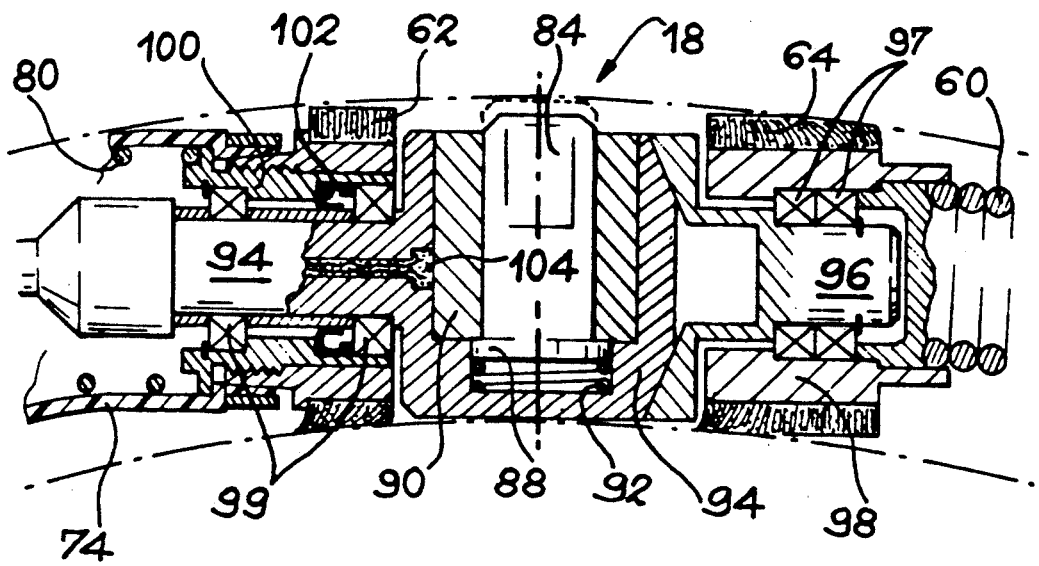

FIG. 3 A sectional view diagrammatically and partially illustrating another embodiment of the probe according to the invention, permitting an inspection of bent tubes by eddy currents.

The probe according to the invention and diagrammatically shown in FIG. 1 is used for the ultrasonic inspection of bent tubes. It is designed so that it can be introduced into these bent tubes, such as the tube 2 in FIG. 1 and has a cable 4 and a probe head 6, which is fixed to one end of the cable 4.

The probe head 6 comprises three articulated modules 8, 10 and 12, the modules 8 and 10 being joined by a cardan joint 14, whilst the modules 10 and 12 are joined by a cardan joint 16. The module 10 is located between the modules 8 and 12 and the module 12 is that which is introduced first into the tube 2. This module 12 comprises an inspection head 18, which is shown in greater detail in FIG. 2, as well as a support 20 on which the inspection head is mounted in rotary manner.

This inspection head 18 has a transmitting-receiving ultrasonic transducer 22 and a mirror 24 able to reflect the ultrasonics, which is positioned facing the transducer 22 and which forms a rigid assembly therewith. More precisely, the transducer 22 is tightly fixed, e.g. by bonding, in a recess made in a case 26.

The requisite seal is in the represented embodiment a water seal, the water being used for the propulsion of the probe in the tube 2 and for the coupling between the transducer, the mirror and the inner wall of the tube to be inspected.

Obviously, the active face of the transducer used for the transmission and reception of ultrasonics, faces the outside of the case 26.

A rotary shaft 28 forming the rotation shaft of the inspection head is fixed on the one hand to the cardan joint 16 and on the other in a bore made in the case 26 and which extends the transducer recess.

The mirror 24 is fixed to a mirror holder 30 having two coaxial rings 32, 34 connected by two clips 36 parallel to the shaft 28, the rings 32, 34 and the shaft 28 being coaxial. The ring 32 is fixed to the periphery of the case 26 on the side of the mirror 24 and the ring 34 is fixed to the periphery of the mirror 24.

A shaft 38, rigidly integral with the ring 34 is aligned with the shaft 28 and forms an extension thereof. The shaft 38 is mounted in rotary manner in a body 40 via two ball bearings 42, 44. The case 26 is mounted in rotary manner in the support 20 by means of two ball bearings 46, 48. A water-tight dynamic joint 50 is provided between the support 20 and the case 26.

An electrical connection 52 for transmitting control signals from the transducer and inspection signals supplied by the latter, traverses the case 26 and passes out of the same on the side of the cardan joint 16.

The mirror 24 transmits to the inner wall of the tube 2 the ultrasonics emitted by the transducer 22 and reflects towards the latter the ultrasonics then returning from the tube.

In the represented embodiment, the mirror has two facets 54, 56, which pass the ultrasonics emitted by the transducer respectively towards the front and the rear, in order to inspect circumferential faults of the inner skin in the vicinity of the not shown welds of the tube 2 by means of Rayleigh waves. The two facets 54, 56 make it possible to examine the two sides of a weld as a function of the probe position (the ultrasonic beam from the transducer not passing through a weld bead).

FIG. 1 shows that the module 12 also has a centring ball 58 for the probe head in the tube 2, said ball being fixed to the body 40 by means of a helical spring 60.

FIG. 2 shows that the module 12 is also provided with means 62, 64 for centring the inspection head in the tube 2. These means 62, 64 can be elastic shoes or brushes and are respectively fixed to the periphery of the support 20 and to the periphery of the body 40.

The module 10 of the probe head is a rotary collector, whilst the module 8 successively comprises, passing from the cardan joint 14 to the cable 4, a motor 66 provided with a not shown reduction gear, an encoder 68, a coil 70 and electronic means 72 for preamplifying inspection signals supplied by the transducer 22 and for exciting the latter (by means of control signals from appropriate means outside the tube 2).

The rotary collector 10 transmits the rotary movement from the motor 66 to the inspection head 18, as well as the electrical connection between the transducer 22 and the associated electronic means 72 (excitation of the transducer and return of the inspection signals therefrom).

This rotary collector 10 is e.g. that marketed by the MORS company under the name "capsule rotary contact" and which has a stator and a rotor, whose shaft issues on either side of the stator, the two ends of said shaft being respectively connected to the cardan joints 14 and 16.

Therefore the rotation of the motor 66 is transmitted to the inspection head via the cardan joint 14, the rotor of the rotary collector 10, the cardan joint 16 and the rotary shaft 28.

The motor 66 is e.g. a direct current micromotor. The encoder 68 equipping the motor 66 is e.g. an optical encoder.

It permits the servocontrol of the rotation speed of the motor and therefore the inspection head, as well as the determination of the circumferential extension of faults which may be observed in the tube by means of ultrasonics.

The electronic means 72, which are connected to the transducer 22 by an electrical connection, are also integral with the coil 70, which is provided in order to reveal by means of eddy current faults in the members associated with the tube 2 (holding U-links and combs for said tube 2), as well as the weld beads of the tub, so that, in association with a millimetric encoder such as that described in document (2), it is possible to accurately determine the position of the transducer 22 in the tube 2, when the probe head has been brought in the latter up to a certain distance (e.g. 100 m) from the end of the tube by which the probe has been introduced.

An electrical connection is provided in the cable 4 for supplying the coil 70 with alternating current and for the transmission to appropriate processing means, located outside the tube 2, the signals from the coil 70.

The probe shown in FIG. 1 also has a sheath 74, which is flexible in flexion and rigid in torsion and which, in the represented embodiment, is also watertight and electrically insulating. It is e.g. a silicone sheath formed on a braided support. The sheath 74 traps that part of the probe head passing from the electronic means 72 up to the support 20.

One end of the sheath 74 is tightly fixed by appropriate means 76 to the periphery of the end of the cable 4 closest to the probe head.

The sheath fixing means 76 e.g. comprise an inner envelope, which traps said end of the cable and an outer envelope, the end of the sheath being trapped between these two envelopes. The other end of the sheath is tightly fixed to the periphery of the support 20 (FIG. 2). The dynamic joint 50 prevents water from penetrating the sheath 74.

The sheath 74 ensures the electrical insulation of the members (motor 66, encoder 68, coil 70, electronic means 72, rotary collector 10) which it contains, in the considered case of probe propulsion by water.

The sheath 74 also permits the displacement of the probe head in the tube 2 on pulling on the cable 4.

Helical springs 78, 80 are placed in the sheath 74 and respectively surround the cardan joints 14, 16. The springs 78 and 80 are provided in order to prevent a crushing of the sheath at the cardan joints, which would damage the sheath during the hydraulic pressurizing of the tube 2.

The cable 4 constantly projects beyond the end of the tube by which the probe head has been introduced and optionally serves as a traction cable for removing the probe head from the tube and also provides the various electrical connections necessary for the operation of the probe shown in FIG. 1, namely the transmission of activation signals for the motor 66, the transducer 22 (via electronic means 72) and the coil 70, as well as signals from the transducer 22 (via electronic means 72), the coil 80 and the encoder 68.

The cable 4 is a composite cable having a central fibre made from Kevlar (registered trademark), which is not shown, and electrical conductors 81 permitting the aforementioned electrical connections.

Not shown balls, moulded to the cable 4, permit the centring of the latter in the tube 2, a reduction of friction against the inner wall of the tube 2 and a uniform distribution of the thrust exerted by the water during the introduction of the probe. They are identical to the "floats" 76 described in document (2).

Not shown control and processing means outside the tube 2 make it possible to use the probe shown in FIG. 1 and in particular introduce the said probe into the tube 2 by means of a water flow 82, the retraction of the probe, the control of the motor 66, the control of the transducer 22, the processing of the signals received from the probe head and in particular from the transducer.

The ultrasonic inspection head 18 shown in FIG. 2 can be replaced by any other inspection head incorporating a radial measuring sensor and in particular by an eddy current inspection head 18, as is diagrammatically shown in FIG. 3.

FIG. 3 shows an eddy current measuring coil 84, which is mounted on a part 88 located in a coil holder 90.

A spring 92 compressed between the bottom of the coil holder 90 and the bottom of the part 88 makes it possible to immobilize the latter in the coil holder by engaging a peripheral shoulder of the part 88 against an inner shoulder of the coil holder 90.

One side of the latter is joined to a rotary shaft 94, which is the homologue of the shaft 28 of FIG. 2, whilst the other side of the coil holder 90 is connected to another shaft 96, aligned with the shaft 94 and which is the homologue of the shaft 38 in FIG. 2. This shaft 96 is mounted in rotary manner in a body 98 via ball bearings 97. The body 98 is extended by a helical spring 60, which is terminated by a not shown centring ball.

The shaft 94 is mounted in rotary manner by means of ball bearings 99 in a support 100, which is the homologue of the support 20 in FIG. 2. The axis of the coil 84 is perpendicular to the rotation of the inspection head 18, defined by the rotating shaft 94.

On their periphery, the support 100 and the body 98 are provided with centring means like means 62 and 64 in FIG. 2. Obviously, the shaft 94 is connected to the cardan joint 16 (FIG. 1).

In the probe partly shown in FIG. 3, use is once again made of a sheath which is flexible in flexion and rigid in torsion and which is of the same type as the sheath 74 in FIG. 1, whose one end is tightly fixed to the periphery of the support 100 and which once again ensures the electrical insulation of the members located within said sheath (particularly the rotary collector and motor).

A water-tight dynamic joint 102 is provided between the shaft 94 and the support 100.

Obviously electrical connections are provided for exciting the coil 84 and for transmitting the signals supplied by the latter, once again via the rotary collector 10 of the probe head (FIG. 1). Moreover, as shown in FIG. 3, the shaft 94 has an axial passage for these electrical connections. This axial passage is tightly sealed, e.g. by means of a tight resin 104 poured into the said passage.

We claim:

1. Bent tube inspection probe for ultrasonically inspecting a tube said probe comprising a cable having electrical conductors and a probe head fixed to one end of the cable, with said probe head comprising: an inspection head, means for transmitting and receiving tube inspection signals; support means for rotationally mounting said inspection head (18); a motor for rotating said inspection head relative to said support means; an encoder connected to the motor for detecting the presence of faults in said tube and a rotary collector positioned between the motor and said support means to ensure a mechanical connection between the motor and the inspection head and to transmit electrical control signals for controlling the transmitting and receiving means and electrical signals from said transmitting and receiving means, with said probe further comprising articulated mechanical connections disposed between the motor and the rotary collector and between the rotary collector and the inspection head and a sheath flexible in flexion and rigid in torsion for joining said support, to said motor and to said rotary collector to prevent relative circumferential displacement thereof.

2. Probe according to claim 1, characterized in that said means for transmitting and receiving tube inspection signals comprises an ultrasonic transmitting-receiving transducer, and ultrasonic reflection means located in a position facing the transducer (22) and being integral therewith for reflecting ultrasound emitted by the transducer towards the tube and for reflecting to the transducer the ultrasound from the tube.

3. Probe according to claim 1, characterized in that said means for transmitting and receiving tube inspection signals comprises a transmitting-receiving coil for transmitting and receiving eddy current signals.

4. Probe according to claim 1, characterized in that the probe head also comprises an auxiliary coil for revealing eddy current discontinuities of the tube or of its environment, thus permitting the identification of the position of the inspection head in the tube.

5. Probe according to claim 1, characterized in that said probe is displaced in the tube (2) by water flow means.

6. Probe according to claim 2, characterized in that said water flow means directs a water flow to couple said transducer, reflection means and the inner wall of the tube (2).

7. Probe according to claim 1, characterized in that the sheath is electrically insulating and traps at least that part of the probe head from the motor to the support at which the inspection head is mounted in rotary manner.

8. Probe according to claim 1, characterized in that the sheath is made from elastomeric material and formed on a braided support.

9. Probe according to claim 8, characterized in that the elastomeric material is silicone.

10. Probe according to claim 1, characterized in that each of the mechanical connections between the motor and the rotary collector and between the latter and the inspection head comprises a homokinetic joint.

* * * * *